United States Patent [19]

Andrews et al.

[11] Patent Number: 4,506,665
[45] Date of Patent: Mar. 26, 1985

[54] ANESTHETIC SUPPLY VALVE AND ADAPTER FOR MASKS

[76] Inventors: E. Trent Andrews, 2 Northgate Dr., San Francisco, Calif. 94127; Steve R. Lamb, 2772 Sydney Way, Castro Valley, Calif. 94546; Robert R. Moore, 4010 East Ave., Hayward, Calif. 94542

[21] Appl. No.: 457,125

[22] Filed: Jan. 11, 1983

Related U.S. Application Data

[63] Continuation-in-part of Ser. No. 268,918, Jun. 1, 1981, abandoned.

[51] Int. Cl.³ ............................................. A61M 16/00
[52] U.S. Cl. .......................... 128/202.27; 128/203.29; 128/205.25; 128/912
[58] Field of Search ..................... 128/202.27, 207.14, 128/207.15, 207.16, 912, 910, 203.29, 205.25, 205.24, 207.12; 251/149.6

[56] References Cited

U.S. PATENT DOCUMENTS

| | | | |
|---|---|---|---|
| 1,005,816 | 10/1911 | Drager | 128/202.27 |
| 1,109,318 | 9/1914 | Browne et al. | 128/203.29 |
| 2,449,165 | 9/1948 | Heidbrink | 128/203.12 |
| 3,004,777 | 10/1961 | Buonaccorsi | 128/203.12 |
| 3,021,840 | 2/1962 | Hallamore et al. | 128/200.21 |
| 3,199,831 | 8/1965 | Sully | 251/149.6 |
| 3,433,222 | 3/1969 | Pinto | 128/204.26 |
| 3,486,730 | 12/1969 | Potash | 128/202.27 |
| 3,862,635 | 1/1975 | Harautuneian | 128/207.15 |
| 3,995,626 | 12/1976 | Pearce, Jr. | 128/202.27 |
| 4,276,876 | 7/1981 | Hakkinen | 128/205.24 |

FOREIGN PATENT DOCUMENTS 812348  2/1937  France ............................ 128/202.27

Primary Examiner—Henry J. Recla
Attorney, Agent, or Firm—Bielen & Peterson

[57] ABSTRACT

An adapter and valve kit for replacement of a conventional anesthetic mask fitting, the adapter connecting to the anesthetic supply orifice of the mask and providing a quick disconnect coupler to a valve fitting, the valve fitting having a spring loaded poppet valve activated by a plunger which contacts and is displaced by the adapter on connection to the valve fitting whereby the poppet valve is open on connection to the adapter and closed on separation from the adapter.

10 Claims, 7 Drawing Figures

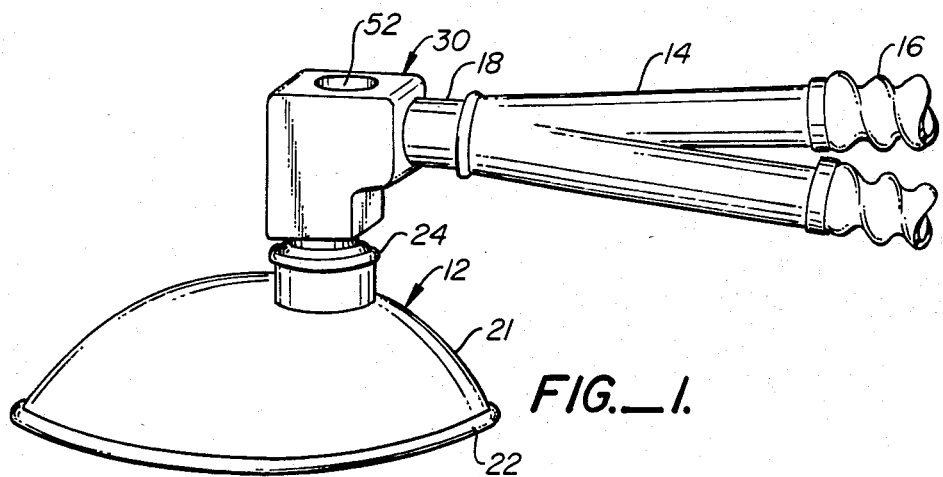
FIG._1.
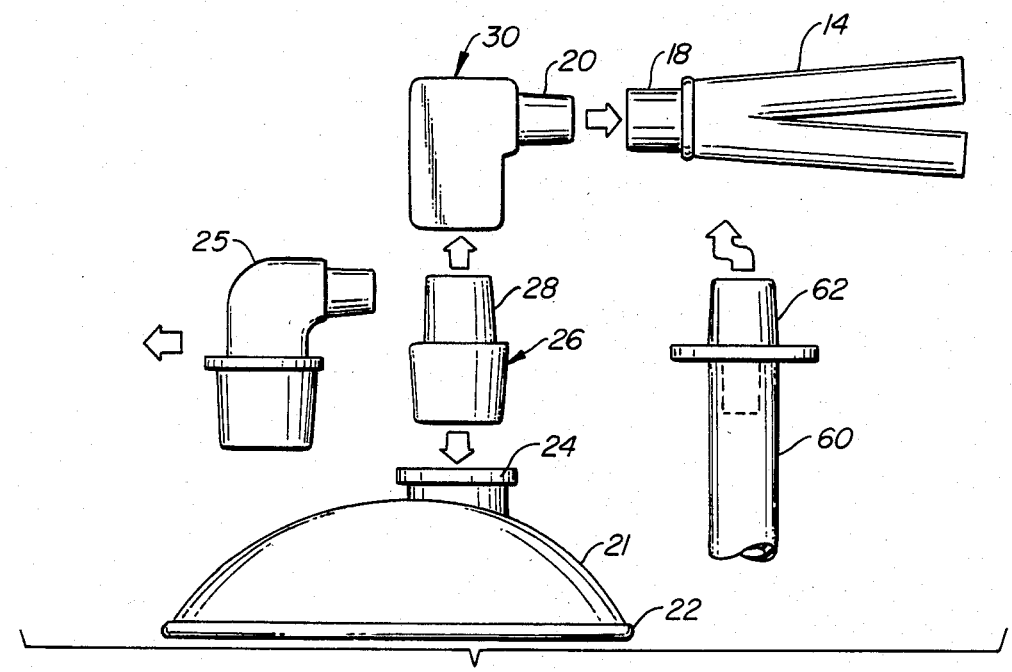
FIG._2.
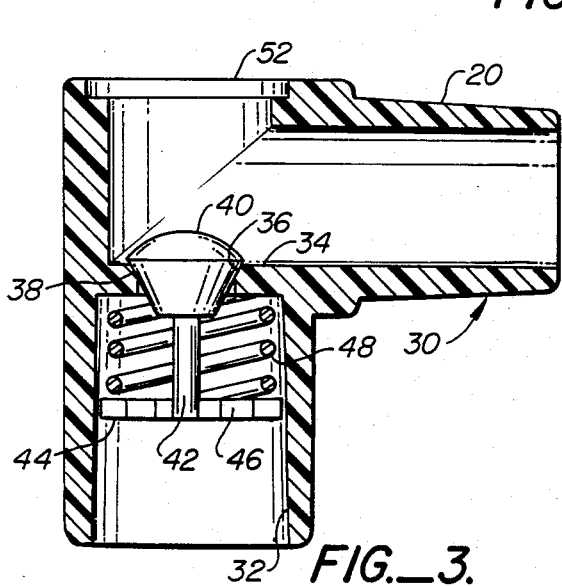
FIG._3.
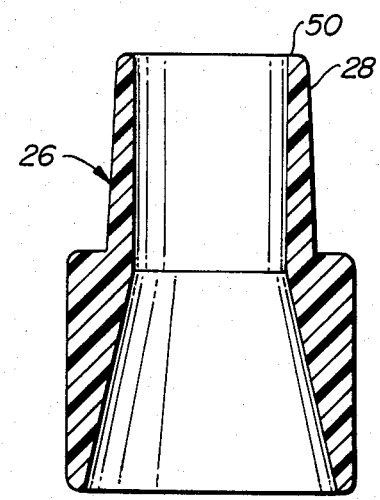
FIG._4.

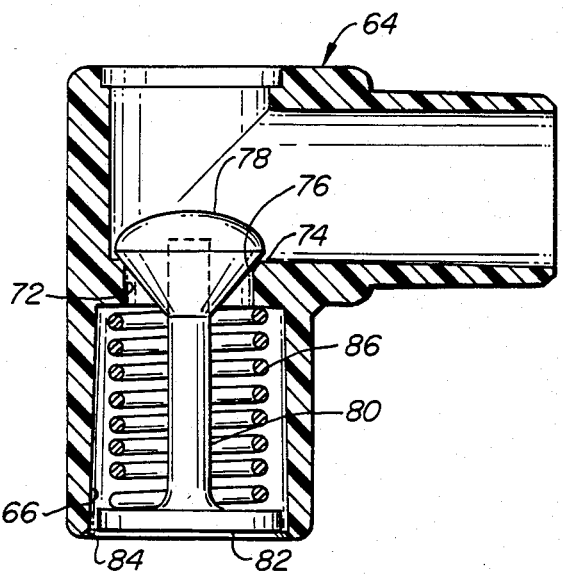
FIG._5.
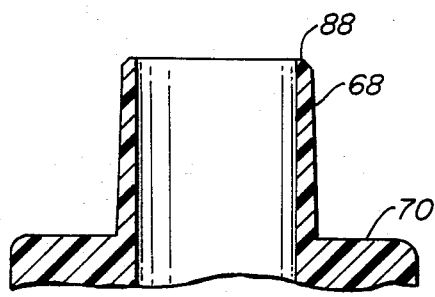
FIG._6.
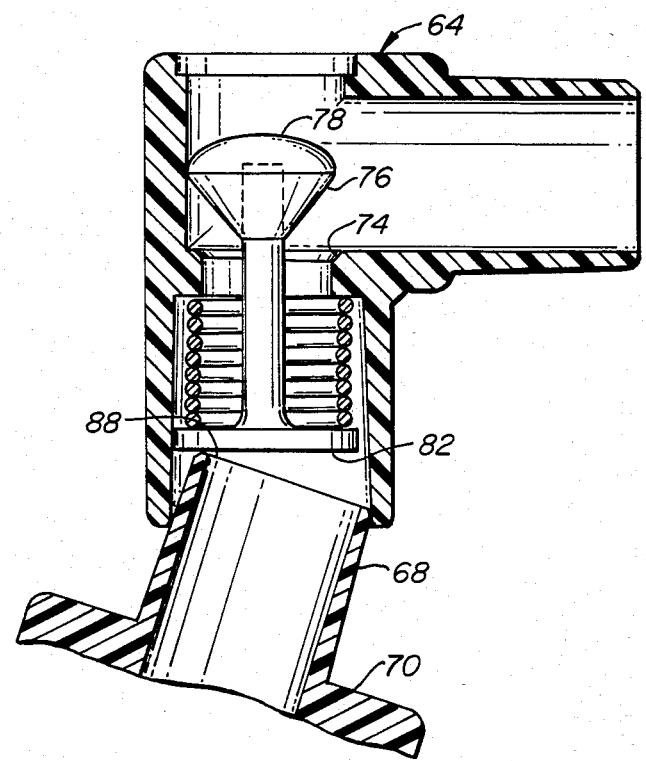
FIG._7.

ANESTHETIC SUPPLY VALVE AND ADAPTER FOR MASKS

This application is a continuation-in-part of our application Ser. No. 06/268,918, filed June 1, 1981 and now abandoned.

BACKGROUND OF THE INVENTION

This invention relates to a valve kit for replacing a conventional elbow fitting connecting anesthetic supply hoses to the anesthetic mask.

In order to maintain sterile conditions in the operating room, it has become the accepted practice to utilize as many disposable items as possible. Because of the problems of decontamination and sterilization, the expense of maintaining many items in a sterile condition often exceeds the cost of the item. This is particularly true for anesthetic masks and immediately associated components which receive a high degree of contamination from intimate patient contact, yet are of a nature that can be inexpensively fabricated and easily disposed. Apparently because of the desire to minimize costs of this disposable item little consideration has been given to relieving annoying conditions attendant in the use of conventional equipment. While there are certain advantages to components of simple design, in the avoidance of system failure, certain conditions in the use of the conventionally designed anesthetic mask exceeds annoyance and poses a danger to both patient and operating room staff.

It is the practice in administering an anesthetic to a patient via a face mask to simply set the mask and supply hose aside to an immediately accessible location, for example, on the patient's chest, when it is desired to examine the patient's mouth to insure a clear passage or to temporarily withdraw anesthetic gas from the patient. In the procedure where the mask is withdrawn for replacement with an endotrachial tube, the mask is necessarily left unattended while preparation of the patient and insertion of the tube is accomplished. During these periods, which are intended to be brief and temporary, the anesthetic gas continues to flow through the hoses and mask and into the operating rooms. Occasionally, the patient requires coincident emergency attention which may divert notice of the condition of the anesthetic mask, causing unacceptable amounts of gas to flow into the operating room. The anesthetic gas may adversely affect the health of the patient or the judgment of the operating staff, and is an occurance to be avoided.

While anesthetic systems have shut-off valves at the gas supply source, these shut-offs are not conveniently located and are often ignored during intended brief removals of the mask. Replacement of the mask with the endotrachial tube is always intended to be brief and would only be complicated by inconvenient valve manipulations. Because such valves often regulate the level of flow as well as on-off conditions, the valves are sometimes avoided because of the requirement for resetting to the desired level once gas is to be readministered. Further, the time delay and removal of attention by the attendant from the patient when making adjustments in the supply valves tends to encourage allowing gases to continue flowing.

While certain valve systems have been considered by applicants, for example, a simple stopcock, it is apparent that most valve systems lack clear indicia of whether the system is on or off. In the high stress environment of the operating room, this is necessary to prevent an inadvertent error.

The valve system of this invention is devised for location at the mask site for convenience and is activated for gas flow only when connected to a mask or a substituted trachea tube. When separated from mask or endotrachial tube, the valve is in an off condition, the separation providing the clear indicia of the state of the valve.

SUMMARY OF THE INVENTION

This invention relates to a mask adapter and valve coupler for replacing a conventional anesthetic mask fitting with a quick disconnect coupler comprising an actuator adapter that connects the anesthetic face mask and a valve fitting that connects to the terminal fitting of the anesthetic gas supply hoses. The coupler on disconnect activates a closure poppet in the valve fitting to prevent the flow of gas. The adapter and valve kit is constructed to adapt to a conventional endotrachial tube in a complimentary manner as the modified mask to allow substitution of the endotrachial tube for the mask. The substituted endotrachial tube has identical operating characteristics for actuation and opening of the valve on connection and closure of the valve on disconnect.

In order for a valve system to be adaptable for operating room use it must be inexpensive and incorporate sufficient safeguards to be free of possible malfunction. The valve coupler of the present invention satisfies these criteria.

The adapter for the mask comprises a fitting having a first plug end which is constructed to fit the gas supply orifice of the anesthetic mask after removal of the standard elbow fitting. The adapter has a second connecting and actuating end which comprises a sloped male coupler having a taper compatible with standard medical fittings which concurrently connects to and actuates a valve fitting.

The valve fitting is constructed in a 90° elbow configuration to match the standard elbow being replaced. However, the replacement elbow includes an internal poppet valve which is actuated by the sloped coupler end of the adapter when inserted into a complimentary sloped female coupler of the valve fitting. The coupler end of the adapter contacts a plunger connected to a spring loaded poppet and upon insertion to a secure connection point, displaces the plunger and connected poppet displacing the poppet from a valve seating, thereby opening a passage for gas flow.

During use the attendant simply disconnects the mask from the valve fitting either prior to the endotrachial tube change-over or at any time it is desired to temporarily discontinue use of the mask. The state of disconnect provides a clear and obvious indication that the mask is not receiving gas. The use of a tapered connector, common in operating room equipment, is simple and comprises a connecting means with which the attendant is readily familiar.

Upon reconnection of the mask or on substitute connection of a conventional endotrachial tube with an identical connector, the valve means is actuated and gas flow resumed.

These and other features will become apparent upon a consideration of the detailed description of the preferred embodiment.

BRIEF DESCRIPTION OF THE DRAWING

FIG. 1 is a perspective view of the coupler in use with a conventional mask.

FIG. 2 is an exploded assembly view of the coupler, mask and replaced prior art elbow fitting.

FIG. 3 is a cross sectional view of the valve member.

FIG. 4 is a cross sectional view of the adapter member.

FIG. 5 is a cross sectional view of an alternate embodiment of a valve member.

FIG. 6 is a cross sectional view partially fragmented, of a connector.

FIG. 7 is a cross sectional view of the valve member and connector in a misaligned connection.

DETAILED DESCRIPTION OF THE PREFERRED EMBODIMENT

Referring to FIG. 1, the adapter and valve coupler, designated as a unit by the reference numeral 10, is shown connecting a conventional anesthetic mask 12 and a conventional Y-fitting 14. The Y-fitting provides the conveyance or mix point for gases generally oxygen and an anesthetic supplied through flexible hoses 16 from a supply source (not shown). The proximate location to the mask allows rapid control of the supply. For example, if anesthetis is stopped and oxygen initiated, only a small quantity of anesthetic remains in the fitting. Purge of an entire length of common hose is not required before the oxygen reaches the patient.

The Y-fitting has a female connector end 18 with an internal taper that connects to a male connector end 20, (FIG. 2), on the valve coupler 10.

The anesthetic mask 12 comprises a domed shaped shield 21 with a cushioned edge 22 that is placed against the face of a patient, as shown, covering both the patient's nose and mouth. The mask 12 includes an orifice structure 24 through which the gases pass for inhalation by the patient. The orifice structure 24 of the mask conventionally connects to an elbow fitting 25 which in turn connects to the Y-fitting 14 as conceptually illustrated in the exploded assembly view of FIG. 2. On substitution of the invented coupler unit 10, the orifice structure connects to an adapter member 26. The connection of the orifice structure and adapter member is a fixed connection and, if desired, can be secured by an adhesive.

The adapter member 26 has a tapered male connector end 28 which connects to and is easily detachable from a valve member 30 of the coupler unit 10. The valve member 30 has a 90° elbow configuration to comply with the accepted connector arrangement in which the coupler is installed. The 90° elbow configuration maintains a low hose profile over the patient. However, the basic concepts described herein can be applied to a fitting having, for example, a straight line or 45° connection.

Referring to FIG. 3, the valve member 30 has an internal, tapered female connector sleeve 32 which couples to the connector end 28 of the adapter member 26, shown also in FIG. 4. The valve member 30 has an internal valve seat structure 34 with a chamfered sealing 36 that engages a sloped surface 38 of a displaceable poppet 40. The poppet has an extension neck dowel 42 which projects into the sleeve 32 of the valve member 30 and is joined to a contact plunger 44, which comprises an actuation member for the valve operation. The plunger comprises a perforated disk with a plurality of holes 46 to allow free passage of gases thereby and engages a compression spring 48 arranged in compression between the plunger 44 and the valve seat structure 34 to bias the poppet 50 in a closed position. The plunger is positioned in the valve sleeve to contact the distal end 50 of the tapered connector end 28 of the adapter member when the adapter member is coupled to the valve member. On coupling, the plunger, and hence the poppet, are displaced by actuation of the connector end of the adapter member unseating the poppet from its valve seating and allowing a through passage for the gases.

To aid in fabrication and assembly of the valve member 30, the member includes a plug 52 which is placed and secured, for example, by epoxy to an inset 54 at the top portion 56 of the valve member. In this manner, the housing of the valve member can be fabricated from a plastic in an injection moulding process, enabling the valve member to be low in cost and hence discardable. The plug poppet, plunger, neck element and if desired, the compression spring, can be fabricated from plastic material to minimize costs. The adapter member is designed for simple fabrication by an injection moulding process.

In use, the conventional elbow fitting 25 is removed and the adapter member 26 installed onto the mask in place of the elbow. The valve member is connected to the Y-fitting before or after connection to the mask and adapter member depending on the state of gas flow. The mask and installed adapter member are easily connected to the valve member. The taper of the connector end of the adapter member and complimentary taper in the valve member sleeve provide a sealed secure connection that can be easily separated as desired. Alternately, a complimentary delivery component for delivering gas to a patient may replace the mask. For example, an endotrachial tube 60 with an identical connector end 62 to the adapter can be connected to the valve member to open the gas flow passage to the respiratory system of the patient.

As the operator understands that gas will not flow with the valve member connected to the Y-fitting without connection of the adapter member or similar component such as the endotrachial tube, he can adjust his procedure accordingly and with assurance regarding the state of the gas flow.

Referring to FIG. 5 an improved valve member 64 is shown. The valve member has a substantially identical construction to the valve member 30 of the prior description. However, it has been discovered that in certain remote instances, the valve member 30 can become partially disconnected from the adapter member 26 or the connector of a delivery component, wherein the poppet is closed and the passage from the valve to delivery component is not breached to atmosphere. In such situation the patient is in a danger of suffocating if the condition is not promptly corrected. The improved valve member 64 eliminates this deleterious possibility by critical modification of the internal structure of the valve member 64.

As shown in FIG. 5, the valve member 64 has an internal tapered female connector sleeve 66 that is constructed to receive the external tapered male end 68 of a connector 70 (shown only in part in FIG. 6) for an adapter or a delivery component anesthetic mask or trachial tube. The mutually conforming taper of the female connector sleeve 66 and the male connector end allows a quick connect or disconnect to be performed without complication. However, if the components are not properly aligned, it is possible to force the male connector end into the female sleeve at an angle and join the components together without the male connector end penetrating a substantial distance into the female sleeve. In such instance, the valving elements must nevertheless be actuated to permit an adequate flow of gas through the valve member and the delivery component to the patient. Alternately, the make connector must be so inadequately coupled that there is either a supplemental breach to atmosphere, or the male connector end is discharged from the female sleeve 66.

These objectives are achieved by the improved valve member shown in FIG. 5. The valve member 64 includes an internal valve seat structure 72 with a chamfered sealing 74 for seating a sloped surface 76 of a displaceable poppet 78. The poppet 78 has an elongated stem 80 which is joined to a plunger 82 that is located at the opening 84 of the connector sleeve in the closed or inactivated position of the poppet 78.

The composite poppet, stem and plunger, member is maintained in the closed position by action of a compression spring 86 which is positioned around the poppet stem 80 with ends biased against the underside of the valve seat structure 72 and the backside of the plunger 82.

In this manner even slight penetration by the male connector end will displace the poppet from its seat. Because of the tapered design of the female sleeve and male connector end, the distal outer rim 88 of the connector has a smaller diameter than the diameter of the opening 84 of the sleeve 66. This diameter difference is such that the male connector end will be ejected by the spring action of the plunger, if the connector is aligned and inserted a short distance into the valve member, which distance is insufficient to adequately displace the poppet for minimal respiration requirements. Further, the diameter difference is such that if the connector is improperly connected to the valve member with the male connector end misaligned in the female sleeve as shown in FIG. 7, the inner most portion of the outer rim 88 will engage the plunger and displace the plunger and poppet an adequate distance to enable minimal respiration. The tapered design of the coupling surfaces cooperates with the location of the spring loaded poppet to insure failsafe operation of the valve member.

While on the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An anesthetic supply system, safety valve coupler for selectively connecting a conventional anesthetic hose fitting to anesthetic gas delivery means adapted to be connected to a breathing passage of a patient, said valve coupler comprising:
 anesthetic gas delivery means adapted to be connected to a breathing passage of a patient and having a gas inlet port, an adapter member having a first end including means connected to said gas inlet port of said delivery means and a second end and a fluid passage between said first and second ends; a valve member having a first end with connector means for connecting said valve member to a conventional hose fitting of an anesthetic supply system and a second end with connector means for connecting said valve member to the second end of said adapter member, said valve member including an internal valve means with an acutuator member contacting the second end of said adapter member for opening said valve means on connection of said valve member to the adapter member, and closing said valve means on disconnection of said valve member from the adapter member, said adapter member being proximally located with respect to said delivery means when connected for minimizing gas contamination of the environment when said adapter member and delivery, means are separated.

2. The valve coupler of claim 1 wherein said valve member and said adapter member are supplied as a replacement kit to substitute for conventional fittings in an anesthetic supply system.

3. The valve coupler of claim 1 wherein said second end of said adapter member comprises a tapered male connector and said second end of said valve member comprises a complimentary tapered female connector.

4. The valve coupler of claim 1 wherein said valve means comprises a valve seating structure within said valve member, a poppet constructed to seat on said valve seating structure, and spring means for biasing said poppet against said valve seating structure.

5. The valve coupler of claim 4 wherein said actuator member comprises a plunger structure connected to said poppet, said plunger structure contacting the second end of said adapter member and displacing said plunger structure and connected poppet on connecting the valve member to the second end of said adapter member.

6. The valve coupler of claim 5 wherein a tapered connection is utilized for connecting said valve member to the adapter member whereby quick connection and disconnection is provided.

7. The valve coupler of claim 6 wherein said plunger structure comprises a dowel connected to said poppet and a perforated disk connected to said dowel, the second end of said adapter member contacting said disk.

8. An anesthetic supply system valve coupler for selectively connecting a conventional anesthetic hose fitting to anesthetic gas delivery means adapted to be connected to a breathing passage of a patient, said valve coupler comprising:
 an anesthetic gas delivery means adapted to be connected to a breathing passage of a patient and having a gas inlet port with connection means having an actuator connector end, a valve member having a first end with connector means for connecting said valve member to a conventional hose fitting of an anesthetic supply system and a second end with connector means connecting said valve member in a sealed connection to said connector means of said delivery means; wherein said valve member includes an internal valve means with an actuator member constructed and positioned to contact the actuating connector end of the delivery means and initiate actuation of the valve means on initial connection of said valve member to the delivery means, prior to a sealed connection being effected, wherein said delivery means has an adequate passage, alternately to atmosphere or to an anesthetic supply in all phases of interconnection of said valve member and the delivery means.

9. The valve coupler of claim 8 wherein said internal valve means includes a tapered female connection sleeve with an opening, said actuator member being positioned at said opening wherein the actuating connector end of the delivery means is tapered and constructed to insert into said connection sleeve, the connector end contacting and actuating said actuator member on initial insertion into said sleeve and prior to coupled engagement of said connection sleeve and actuating connector end, said actuator member being biased to eject said actuating connector end of said delivery means on inadequate coupling of said valve member and said delivery means.

10. The valve coupler of claim 9 wherein said valve means includes a displaceable poppet, a poppet seat and a spring biasing said poppet against said poppet seat, wherein said poppet has a stem and a plunger, said plunger being disposed at said opening of said connection sleeve for contact with the tapered connector end of the delivery means an initiating connection of said valve coupler and the delivery means.

* * * * *